(12) United States Patent
Strominger et al.

(10) Patent No.: US 7,566,767 B2
(45) Date of Patent: Jul. 28, 2009

(54) SYNTHETIC PEPTIDES AND METHODS OF USE FOR AUTOIMMUNE DISEASE THERAPIES

(75) Inventors: Jack L. Strominger, Cambridge, MA (US); Masha Fridkis-Hareli, Sudbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 322 days.

(21) Appl. No.: 10/438,538

(22) Filed: May 15, 2003

(65) Prior Publication Data

US 2004/0006022 A1    Jan. 8, 2004

Related U.S. Application Data

(62) Division of application No. 09/359,099, filed on Jul. 22, 1999.

(60) Provisional application No. 60/123,675, filed on Mar. 9, 1999, provisional application No. 60/093,859, filed on Jul. 23, 1998.

(51) Int. Cl.
*A61K 38/00* (2006.01)
*A61K 31/74* (2006.01)
(52) U.S. Cl. .................. 530/326; 530/350; 530/403
(58) Field of Classification Search ............ 530/329, 530/326, 350, 324; 424/185.1; 514/12, 14, 514/16, 2
See application file for complete search history.

(56) References Cited

U.S. PATENT DOCUMENTS

| 3,849,550 A | 11/1974 | Teitelbaum et al. |
| 5,583,031 A | 12/1996 | Stern |
| 5,736,142 A | 4/1998 | Sette et al. |
| 6,514,938 B1 | 2/2003 | Gad et al. |
| 6,800,287 B2 * | 10/2004 | Gad et al. ............... 424/185.1 |
| 2002/0055466 A1 * | 5/2002 | Aharoni et al. ............ 514/12 |
| 2004/0038887 A1 * | 2/2004 | Strominger et al. ......... 514/12 |

FOREIGN PATENT DOCUMENTS

| WO | WO 92/02543 | * | 2/1992 |
| WO | WO 94/00148 | | 1/1994 |
| WO | WO 94/04171 | | 3/1994 |
| WO | WO 94/26774 | | 11/1994 |
| WO | WO 95/26980 | | 10/1995 |
| WO | WO 95/31990 | | 11/1995 |
| WO | WO 95/31997 | | 11/1995 |
| WO | WO 9632119 | | 10/1996 |
| WO | WO 96/40777 | | 12/1996 |
| WO | WO 97/49430 | | 12/1997 |
| WO | WO 98/01581 | | 1/1998 |
| WO | WO 98/05684 | | 2/1998 |
| WO | WO 00/05250 | | 2/2000 |

OTHER PUBLICATIONS

Harlow and Lane. Antibodies. A Laboratory Manual. 1988, Cold Spring Harbor Laboratory, USA, p. 660.*
Ramensee et al. MHC Ligands and Peptide Motifs. Springer, Landes Bioscience, Austin, 1997, pp. 21-25 and 220-221.*
Fridkis-Hareli et al. J. Immunol. 162, pp. 4697-4704, 1999.*
Teitelbaum et al. PNAS USA 85, pp. 9724-9728, 1988.*
Teitelbaum et al. PNAS USA 89, pp. 137-141, 1992.*
Comi and Moiola. Baillier's Clinical Neurology 6(3), pp. 495-509, Oct. 1997.*
Gerritse, K. Peptide applications in autoimmune disease research. Immunological recognition of peptides in Medicine and Biology. Zegers N.D., Boersma W.J.A. & Claassen, E., eds. vol. 20, pp. 269-283, 1995.*
Anderton et al. Immunology. 2001, 104: 367-376.*
Ngo et al. The Protein Folding Problem and Tertiary Structure Prediction, Merz & LeGrand, Birkhauser Boston, pp. 491-495, 1994.*
Li et al (J. Mol. Biol. 2000, 304(2): 177-188).*
Andersson, et al., "Definition of MHC and T cell receptor contacts in the HLA-DR4-restricted immunodominant epitope in type II collagen and characterization of collagen-induced arthritis in HLA-DR4 and human CD4 transgenic mice", Proc. Natl. Acad. Sci. USA, 95: 7574-7579 (1998).
Kropshofer, et al., "Self-Peptides from Four HLA-DR Alleles Share Hydrophobic Anchor Residues Near the $NH_2$-Terminal Including Proline as a Stop Signal for Trimming[1]", The Journal of Immunology, 151:4732-4742 (1993).
Jerry S. Wolinsky, "Copolymer 1: A most reasonable alternative therapy for early relapsing-remitting multiple sclerosis with mild disability", Neurology, 45:1245-1247 (1995).
Bornstein, M., et al., *A Pilot Trial Of Cop 1 In Exacerbating-Remitting Multiple Sclerosis*, The New England Journal of Medicine, vol. 317, No. 7, pp. 408-414, Aug. 13, 1987.
Fridkis-Hareli, M., et al., *Synthetic amino acid copolymers that bind to HLA-DR proteins and inhibit type II collagen-reactive T cell clones*, Proc. Natl. Acad. Sci. USA, vol. 95, pp. 12528-12531, Oct. 1998.
Fridkis-Hareli, M., et al., *Promiscuous Binding of Synthetic Copolymer 1 to Purified HLA-DR Molecules*, The Journal of Immunology, vol. 160, pp. 4386-4397, 1998.
Fridkis-Hareli, M., et al., *Synthetic Copolymer 1 and Myelin Basic Protein Do Not Require Processing Prior to Binding to Class II Major Histocompatibility Complex Molecules on Living Antigen-Presenting Cells*, Cellular Immunology, vol. 163, pp. 229-236, 1995.

(Continued)

*Primary Examiner*—G. R. Ewoldt
*Assistant Examiner*—Marianne DiBrino
(74) *Attorney, Agent, or Firm*—Sonia K. Guterman; Michael I. Falkoff; Lawson & Weitzen, LLP

(57) ABSTRACT

The invention provides peptide compositions, and methods of making and using therapeutic compositions for treatment of a subject for an autoimmune or an inflammatory disease. The invention also provides kits for assaying binding of a composition to a water-soluble MHC protein.

4 Claims, No Drawings

OTHER PUBLICATIONS

Fridkis-Hareli, M., et al., *Direct binding of myelin basis protein and synthetic copolymer 1 to class II major histocompatibility complex molecules on living antigen-presenting cells—specificity and promiscuity*, Proc. Natl. Acad. Sci. USA, vol. 91, pp. 4872-4876, May 1994.

Gerritse, K., *Peptide Applications In Autoimmune Disease Research*, ch. 20 in *Synthetic Peptides in Medicine and Biology*, pp. 269-287.

Johnson, K., et al., *Copolymer 1 reduces relapse rate and improves disability in relapsing-remitting multiple sclerosis: Results of a phase III multicenter, double-blind, placebo-controlled trial*, Neurology, vol. 45, pp. 1268-1276, Jul. 1995.

Rosloniec, E., et al., *An HLA-DR1 Transgene Confers Susceptibility to Collagen-induced Arthritis Elicited with Human Type II Collagen*, The Journal of Experimental Medicine, vol. 185, No. 6, pp. 1113-1122, Mar. 17, 1997.

Teitelbaum, D., et al., *Copolymer 1 inhibits chronic relapsing experimental allergic encephalomyelitis induced by proteolipid protein (PLP) petides in mice and interferes with PLP-specific T cell responses*, Journal of Neuroimmunology, vol. 64, pp. 209-217, 1996.

Teitelbaum, D., et al., *Suppression by several synthetic polypeptides of experimental allergic encephalomyelitis induced in guinea pigs and rabbits with bovine and human basic encephalitogen*, Eur. J. Immunol, vol. 3, pp. 273-279, 1973.

Webb, C., et al., *Molecular Requirements Involved In Suppression Of EAE By Synthetic Basic Copolymers Of Amino Acids*, Immunochemistry, vol. 13, pp. 333-337, 1976.

Weiner, H., *Oral tolerance: immune mechanisms and treatment of autoimmune diseases*, Immunology Today, vol. 18, No. 7, pp. 335-343, Jul. 1997.

Wucherpfennig, K. et al, *Structural Requirements for Binding of an Immunodominant Myelin Basic Protein Peptide to DR2 Isotypes and for Its Recognition by Human T Cell Clones*, J. Exp. Med., vol. 179, pp. 279-290, Jan. 1994.

Fridkis-Hareli, M., et al., "Binding of random copolymers of three aminoacids to class II MHC molecules", International Immunology, vol. 11, No. 5, pp. 635-641, May 1999.

Jemmerson, R., "Epitope Mapping by Proteolysis of Antigen-Antibody Complexes. Protein Footprinting" Methods in Molecular Biology, US, Humana Press Inc., Clifton, NJ, vol. 66, pp. 97-108, 1996.

Li, Q., et al., "Glatiramer acetate blocks the activation of THP-1 cells by interferon-gamma" European Journal of Pharmacology, vol. 342, pp. 303-310, 1998.

Sheshberadaran, H., et al., Protein-antigen monoclonal antibody contact sites investigated by limited proteolysis of monoclonal antibody-bound antigen: protein "footprinting" Proceedings of the National Academy of Sciences of USA, vol. 85, pp. 1-5, 1988.

Sheshberadaran, H., et al., "Protein footprinting method of studying antigen-antibody interactions and epitope mapping" Methods in Enzymology, vol. 178, pp. 746-764.

\* cited by examiner

SEQUENCE LISTING

<160> NUMBER OF SEQ ID NOS: 59

<210> SEQ ID NO 1
<211> LENGTH: 13
<212> TYPE: PRT
<213> ORGANISM: Influenza hemagglutinin

<400> SEQUENCE: 1

Pro Lys Tyr Val Lys Gln Asn Thr Leu Lys Leu Ala Thr
 1               5                  10

<210> SEQ ID NO 2
<211> LENGTH: 13
<212> TYPE: PRT
<213> ORGANISM: Homo sapiens collagen II

<400> SEQUENCE: 2

Ala Gly Phe Lys Gly Glu Gln Gly Pro Lys Gly Glu Pro
 1               5                  10

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays, control collagen
      II bracketed by alanine residues.
<220> FEATURE:
<221> NAME/KEY: SITE
<222> LOCATION: (1)..(15)

<400> SEQUENCE: 3

Ala Ala Gly Phe Lys Gly Glu Gln Gly Pro Lys Gly Glu Pro Ala
 1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays, control influenza
      hemagglutinin bracketed by alanine residues.
<220> FEATURE:
<221> NAME/KEY: SITE
<222> LOCATION: (1)..(15)

<400> SEQUENCE: 4

Ala Pro Lys Tyr Val Lys Gln Asn Thr Leu Lys Leu Ala Thr Ala
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 5

-continued

Ala Ala Ala Tyr Ala Ala Ala Ala Ala Lys Ala Ala Ala Ala
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assay.
<220> FEATURE:
<221> NAME/KEY: SITE
<222> LOCATION: (1)..(15)

<400> SEQUENCE: 6

Ala Glu Lys Tyr Ala Ala Ala Ala Ala Lys Ala Ala Ala Ala
 1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 7

Ala Lys Glu Tyr Ala Ala Ala Ala Ala Lys Ala Ala Ala Ala
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 8

Ala Lys Lys Tyr Ala Ala Ala Ala Ala Lys Ala Ala Ala Ala
 1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 9

Ala Glu Ala Tyr Ala Ala Ala Ala Ala Lys Ala Ala Ala Ala
 1               5                  10                  15

<210> SEQ ID NO 10
<211> LENGTH: 15
<212> TYPE: PRT

```
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 10

Lys Glu Ala Tyr Ala Ala Ala Ala Ala Ala Lys Ala Ala Ala Ala
 1               5                  10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 11

Ala Glu Glu Tyr Ala Ala Ala Ala Ala Ala Lys Ala Ala Ala Ala
 1               5                  10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 12

Ala Ala Glu Tyr Ala Ala Ala Ala Ala Lys Ala Ala Ala Ala Ala
 1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 13

Glu Lys Ala Tyr Ala Ala Ala Ala Ala Ala Lys Ala Ala Ala Ala
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
```

```
<222> LOCATION: (1)..(15)

<400> SEQUENCE: 14

Ala Ala Lys Tyr Glu Ala Ala Ala Ala Lys Ala Ala Ala Ala
  1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 15

Ala Ala Lys Tyr Ala Glu Ala Ala Ala Lys Ala Ala Ala Ala
  1               5                  10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 16

Glu Ala Ala Tyr Ala Ala Ala Ala Ala Lys Ala Ala Ala Ala
  1               5                  10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 17

Glu Lys Lys Tyr Ala Ala Ala Ala Ala Lys Ala Ala Ala Ala
  1               5                  10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 18

Glu Ala Lys Tyr Ala Ala Ala Ala Ala Lys Ala Ala Ala Ala
  1               5                  10                  15
```

```
<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 19

Ala Glu Lys Tyr Ala Ala Ala Ala Ala Ala Ala Ala Ala Ala Ala
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 20

Ala Lys Glu Tyr Ala Ala Ala Ala Ala Ala Ala Ala Ala Ala Ala
 1               5                  10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 21

Ala Lys Lys Tyr Glu Ala Ala Ala Ala Ala Ala Ala Ala Ala Ala
 1               5                  10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 22

Ala Lys Lys Tyr Ala Glu Ala Ala Ala Ala Ala Ala Ala Ala Ala
 1               5                  10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence:Synthetic
``` peptide of predetermined sequence for testing of
        activity in MHC Class II assays.
<220> FEATURE:
<221> NAME/KEY: SITE
<222> LOCATION: (1)..(15)

<400> SEQUENCE: 23

Ala Glu Ala Tyr Lys Ala Ala Ala Ala Ala Ala Ala Ala Ala Ala
 1               5                  10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence:Synthetic
        peptide of predetermined sequence for testing of
        activity in MHC Class II assays.
<220> FEATURE:
<221> NAME/KEY: SITE
<222> LOCATION: (1)..(15)

<400> SEQUENCE: 24

Lys Glu Ala Tyr Ala Ala Ala Ala Ala Ala Ala Ala Ala Ala Ala
 1               5                  10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence:Synthetic
        peptide of predetermined sequence for testing of
        activity in MHC Class II assays.
<220> FEATURE:
<221> NAME/KEY: SITE
<222> LOCATION: (1)..(15)

<400> SEQUENCE: 25

Ala Glu Glu Tyr Lys Ala Ala Ala Ala Ala Ala Ala Ala Ala Ala
 1               5                  10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence:Synthetic
        peptide of predetermined sequence for testing of
        activity in MHC Class II assays.
<220> FEATURE:
<221> NAME/KEY: SITE
<222> LOCATION: (1)..(15)

<400> SEQUENCE: 26

Ala Ala Glu Tyr Lys Ala Ala Ala Ala Ala Ala Ala Ala Ala Ala
 1               5                  10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence:Synthetic
        peptide of predetermined sequence for testing of
        activity in MHC Class II assays.
<220> FEATURE:
<221> NAME/KEY: SITE
<222> LOCATION: (1)..(15)

<400> SEQUENCE: 27

Glu Lys Ala Tyr Ala Ala Ala Ala Ala Ala Ala Ala Ala
 1               5                  10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 28

Ala Ala Lys Tyr Glu Ala Ala Ala Ala Ala Ala Ala Ala
 1               5                  10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 29

Ala Ala Lys Tyr Ala Glu Ala Ala Ala Ala Ala Ala Ala
 1               5                  10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 30

Glu Lys Lys Tyr Ala Ala Ala Ala Ala Ala Ala Ala Ala
 1               5                  10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 31

Glu Ala Lys Tyr Ala Ala Ala Ala Ala Ala Ala Ala Ala
 1               5                  10                  15

<210> SEQ ID NO 32
<211> LENGTH: 15
<212> TYPE: PRT

```
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 32

Ala Glu Tyr Ala Lys Ala Ala Ala Ala Ala Ala Ala Ala Ala Ala
 1               5                  10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 33

Ala Glu Lys Ala Tyr Ala Ala Ala Ala Ala Ala Ala Ala Ala Ala
 1               5                  10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 34

Glu Lys Tyr Ala Ala Ala Ala Ala Ala Ala Ala Ala Ala Ala Ala
 1               5                  10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(15)

<400> SEQUENCE: 35

Ala Tyr Lys Ala Glu Ala Ala Ala Ala Ala Ala Ala Ala Ala Ala
 1               5                  10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
```

```
<222> LOCATION: (1)..(15)

<400> SEQUENCE: 36

Ala Lys Tyr Ala Glu Ala Ala Ala Ala Ala Ala Ala Ala Ala Ala
 1               5                  10                  15

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(4)

<400> SEQUENCE: 37

Glu Lys Val Ala
 1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(4)

<400> SEQUENCE: 38

Glu Lys Phe Ala
 1

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(5)

<400> SEQUENCE: 39

Ala Glu Lys Tyr Ala
 1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(5)

<400> SEQUENCE: 40

Ala Glu Lys Val Ala
 1               5
```

```
<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(5)

<400> SEQUENCE: 41

Ala Glu Lys Phe Ala
 1               5

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(4)

<400> SEQUENCE: 42

Lys Glu Tyr Ala
 1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(4)

<400> SEQUENCE: 43

Lys Tyr Ala Glu
 1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(4)

<400> SEQUENCE: 44

Lys Glu Val Ala
 1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence:Synthetic
```

```
        peptide of predetermined sequence for testing of
        activity in MHC Class II assays.
<220> FEATURE:
<221> NAME/KEY: SITE
<222> LOCATION: (1)..(4)

<400> SEQUENCE: 45

Lys Val Ala Glu
  1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence:Synthetic
        peptide of predetermined sequence for testing of
        activity in MHC Class II assays.
<220> FEATURE:
<221> NAME/KEY: SITE
<222> LOCATION: (1)..(4)

<400> SEQUENCE: 46

Lys Glu Phe Ala
  1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence:Synthetic
        peptide of predetermined sequence for testing of
        activity in MHC Class II assays.
<220> FEATURE:
<221> NAME/KEY: SITE
<222> LOCATION: (1)..(4)

<400> SEQUENCE: 47

Lys Phe Ala Glu
  1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence:Synthetic
        peptide of predetermined sequence for testing of
        activity in MHC Class II assays.
<220> FEATURE:
<221> NAME/KEY: SITE
<222> LOCATION: (1)..(4)

<400> SEQUENCE: 48

Lys Tyr Ala Ala
  1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence:Synthetic
        peptide of predetermined sequence for testing of
        activity in MHC Class II assays.
<220> FEATURE:
<221> NAME/KEY: SITE
<222> LOCATION: (1)..(4)

<400> SEQUENCE: 49
```

Lys Lys Tyr Ala
1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(4)

<400> SEQUENCE: 50

Lys Val Ala Ala
1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(4)

<400> SEQUENCE: 51

Lys Lys Val Ala
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(4)

<400> SEQUENCE: 52

Lys Phe Ala Ala
1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(4)

<400> SEQUENCE: 53

Lys Lys Phe Ala
1

<210> SEQ ID NO 54
<211> LENGTH: 5

```
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(5)

<400> SEQUENCE: 54

Ala Lys Tyr Ala Glu
 1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(5)

<400> SEQUENCE: 55

Glu Ala Lys Tyr Ala
 1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(5)

<400> SEQUENCE: 56

Ala Lys Val Ala Glu
 1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(5)

<400> SEQUENCE: 57

Glu Ala Lys Val Ala
 1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
```

```
<221> NAME/KEY: SITE
<222> LOCATION: (1)..(5)

<400> SEQUENCE: 58

Ala Lys Phe Ala Glu
  1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence:Synthetic
      peptide of predetermined sequence for testing of
      activity in MHC Class II assays.
<220> FEATURE:
<221> NAME/KEY: SITE
<222> LOCATION: (1)..(5)

<400> SEQUENCE: 59

Glu Ala Lys Phe Ala
  1               5
```

SYNTHETIC PEPTIDES AND METHODS OF USE FOR AUTOIMMUNE DISEASE THERAPIES

RELATED APPLICATION

This application is a division of U.S. Ser. No. 09/359,099 filed Jul. 22, 1999, and claims the benefit of U.S. Provisional Application No. 60/093,859 filed Jul. 23, 1998, and U.S. Provisional Application No. 60/123,675 filed Mar. 9, 1999.

GOVERNMENT FUNDING

This invention was made in part with government support under grant CA47554 awarded by the National Institutes of Health. The government has certain rights in the invention.

BACKGROUND

An autoimmune disease results from an inappropriate immune response directed against a self antigen (an autoantigen), which is a deviation from the normal state of self-tolerance. Self-tolerance arises when the production of T cells and B cells capable of reacting against autoantigens has been prevented by events that occur in the development of the immune system during early life. The cell surface proteins that play a central role in regulation of immune responses through their ability to bind and present processed peptides to T cells are the major histocompatibility complex (MHC) molecules (Rothbard, J. B., et al., 1991, *Annu. Rev. Immunol.* 9:527).

A number of therapeutic agents have been developed to treat autoimmune diseases, including general anti-inflammatory drugs such as "super aspirins", for example, agents that can prevent formation of low molecular weight inflammatory compounds by inhibiting a cyclooxygenase; agents that can function by inhibiting a protein mediator of inflammation, for example, by sequestering the inflammatory protein tumor necrosis factor (TNF) with an anti-TNF specific monoclonal antibody or antibody fragment, or with a soluble form of the TNF receptor; agents that target a protein on the surface of a T cell and generally prevent interaction with an antigen presenting cell (APC) by inhibiting the CD4 receptor or the cell adhesion receptor ICAM-1. However, compositions having natural folded proteins as therapeutic agents can incur problems in production, formulation, storage, and delivery. Several of these problems necessitate delivery to the patient in a hospital setting.

An additional target for inhibition of an autoimmune response is the set of lymphocyte surface proteins MHC molecules, particularly a protein encoded by an MHC class II gene, for example, HLA-DR, -DQ and -DP. Each of the MHC genes is found in a large number of alternative or allelic forms within a mammalian population. The genomes of subjects affected with certain autoimmune diseases, for example multiple sclerosis (MS) and rheumatoid arthritis (RA), are more likely to carry one or more characteristic MHC class II alleles, to which that disease is linked.

RA is a common human autoimmune disease with a prevalence of about 1% among Caucasians (Harris, B. J. et al., 1997, *In Textbook of Rheumatology* 898-932), currently affecting 2.5 million Americans. RA is characterized by chronic inflammation of the synovial joints and infiltration by activated T cells, macrophages and plasma cells, leading to a progressive destruction of the articular cartilage. It is the most severe form of joint disease. Inherited susceptibility to RA is strongly associated with the affected subject having at the MHC class II DRB1 locus the allele DRB1*0401, DRB1*0404, or DRB1*0405 or the DRB1*0101 allele. The nature of the autoantigen(s) in RA is poorly understood, although collagen type II (CII) is a prominent candidate. An immunodominant T cell epitope in collagen type II corresponding to residues 261-273 has been identified (Fugger, L., et al., 1996, *Eur. J. Immunol.* 26: 928-933).

It would be desirable to identify agents that were able to bind specifically to one or more of the linked MHC class II molecules and thereby to inhibit an inappropriate immune response. An agent that interacts and binds relatively nonspecifically to several MHC class II molecules is Copolymer 1 (Cop 1), a synthetic amino acid heteropolymer that was shown to be capable of suppressing experimental allergic encephalomyclitis (EAE; Sela, M., R. Arnon, et al., 1990, *Bull. Inst. Pasteur* (Paris)), which can be induced in the mouse and is a model for MS. Cop 1 which is poly(Y,E,A,K), indicated herein "YEAK" using the one letter amino acid code (see infra; Y represents tyrosine, E glutamic acid, A alanine, and K lysine) has been used to treat relapsing forms of MS but does not suppress the disease entirely (Bornstein, M. B., et al., 1987, *N. Engl. J. Med.* 317:408; Johnson, K P., et al., 1995, *Neurology* 45:1268).

There is a need for improved treatments for autoimmune diseases. A potential source of such treatments would be to identify agents that bind selectively to a purified MHC class II allele protein molecule in vitro, particularly to a protein which is a product of an MHC class II allele that is associated with an autoimmune disease. In addition, the agent should also bind to that protein as it occurs on the surfaces of antigen presenting cells in vivo, and thereby can block, anergize, or inactivate T cells that are responsible for the autoimmune disease.

SUMMARY

In one embodiment of the invention, a composition is provided which is a synthetic peptide having an amino acid sequence comprising at least three residues selected from the group of amino acids consisting of aromatic acids, negatively charged amino acids, positively charged amino acids, and aliphatic amino acids, the synthetic peptide being at least seven amino acid residues in length and capable of binding to an MHC class II protein associated with an autoimmune disease. Thus the aromatic amino acid is selected from the group consisting of tyrosine (Y), valine (V), and phenylalanine (F), the positively charged amino acid is lysine (K), and the sequence is selected from the group consisting of lysine-tyrosine (KY), lysine-valine (KV), and lysine-phenylalanine (KF). Even further, in the provided composition the amino acid which is aliphatic is alanine (A), and the sequence is selected from the group of amino acid sequences consisting of glutamic acid-lysine-tyrosine-alanine (EKYA; SEQ ID NO: 60), glutamic acid-lysine-valine-alanine (EKVA; SEQ ID NO: 37), and glutamic acid-lysine-phenylalanine-alanine (EKFA; SEQ ID NO: 38). The composition can further comprise an amino-terminal alanine, and the sequence is selected from the group of amino acid sequences consisting of alanine-glutamic acid-lysine-tyrosine-alanine (AEKYA; SEQ ID NO: 39), alanine-glutamic acid-lysine-valine-alanine (AEKVA; SEQ ID NO: 40), and alanine-glutamic acid-lysine-phenylalanine-alanine (AEKFA; SEQ ID NO: 41). The synthetic peptides that are the embodiments of the invention are capable of binding to an MHC class II protein associated with an autoimmune disease, for example, an arthritic condition, for example, rheumatoid arthritis. In another embodiment, the synthetic peptide composition which is an embodiment of the invention has aliphatic amino acid which is alanine, and the amino acid sequence is selected from the group of sequences consisting of: lysine-glutamic acid-tyrosine-alanine (KEYA; SEQ ID NO: 42), lysine-tyrosine-alanine-glutamic acid (KYAE; SEQ ID NO: 43), lysine-glutamic acid-valine-alanine (KEVA; SEQ ID NO: 44), lysine-valine-alanine-glutamic acid (KVAE; SEQ ID NO: 45), lysine-glutamic acid-phenylalanine-alanine (KEFA; SEQ ID NO: 46), and lysine-phenylalanine-alanine-glutamic acid (KFAE; SEQ ID NO: 47). In a further embodiment wherein the aliphatic amino acid is alanine (A), the amino acid sequence is selected from the group of amino acid sequences consisting of lysine-tyrosine-alanine-alanine (KYAA; SEQ ID NO: 48) or lysine-lysine-tyrosine-alanine (KKYA; SEQ ID NO: 49), lysine-valine-alanine-alanine (KVAA; SEQ ID NO: 50) or lysine-lysine-valine-alanine (KKVA; SEQ ID NO: 51), lysine-phenylalanine-alanine-alanine (KFAA; SEQ ID NO: 52), and lysine-lysine-phenylalanine-alanine (KKFA; SEQ ID NO: 53). In this embodiment, the peptide can further comprise two alanine residues, and the sequence can be selected from the group of sequences consisting of alanine-lysine-tyrosine-alanine-glutamic acid (AKYAE; SEQ ID NO: 54), glutamic acid-alanine-lysine-tyrosine-alanine (EAKYA; SEQ ID NO: 55), alanine-lysine-valine-alanine-glutamic acid (AKVAE; SEQ ID NO: 56), glutamic acid-alanine-lysine-valine-alanine (EAKVA; SEQ ID NO: 57), alanine-lysine-phenylalanine-alanine-glutamic acid (AKFAE; SEQ ID NO: 58); and glutamic acid-alanine-lysine-phenylalanine-alanine (EAKFA; SEQ ID NO: 59). The peptide composition of this embodiment of the invention can be 7-100 amino acid residues in length.

Another embodiment of the invention provides a composition which is a synthetic peptide having therapeutic activity in a subject suffering from an autoimmune disease, and the amino acid sequence having at least one of each of amino acids glutamic acid, lysine, and alanine and an amino acid selected from the group consisting of tyrosine, valine, and phenylalanine. The composition can be a peptide which is 7-100 amino acids in length, for example, 7-50 amino acids in length, 7-25 amino acids in length, and 7-15 amino acids in length. The composition can be formulated as a unitary dosage in a pharmaceutically acceptable carrier, for example, a synthetic peptide which is substantially pure. An embodiment of the invention is a synthetic peptide having greater affinity for the antigen binding groove of an MHC class II protein associated with the autoimmune disease than a type II collagen 261-273 peptide. In a further example of these embodiments, a composition is provided comprising an amino acid analog at the residue locations and in an amount protease degradation of the peptide in the subject.

Another embodiment of the invention is an isolated peptide composition having a sequence selected from the group consisting of: AKEYAAAAAAKAAAA (SEQ ID NO: 7), AAEYAAAAAAKAAAA (SEQ ID NO: 12), AAKYAEAAAAKAAAA (SEQ ID NO: 15), and EAKYAAAAAA-KAAAA (SEQ ID NO: 18). A further embodiment of the invention is an example of one of the preceding isolated peptides in which the tyrosine (Y) has been substituted by a valine (F) or a phenylalanine (F). Further, an embodiment of the invention can be an isolated peptide composition having a sequence selected from the group consisting of: AEKYAAAAAAKAAAA (SEQ ID NO: 6), AKEYAAAAAAKAAAA (SEQ ID NO: 7), KEAYAAAAAAKAAAA (SEQ ID NO: 10), AEEYAAAAAAKAAAA (SEQ ID NO: 11), AAEYAAAAAAKAAAA (SEQ ID NO: 12), EKAYAAAAAAKAAAA (SEQ ID NO: 13), AAK-YEAAAAAAKAAAA (SEQ ID NO: 14), AAKYAEAAAA-KAAAA (SEQ ID NO: 15), EAAYAAAAAAKAAAA (SEQ ID NO: 16), EKKYAAAAAAKAAAA (SEQ ID NO: 17), EAKYAAAAAAKAAAA (SEQ ID NO: 18), AKK-YEAAAAAAAAAA (SEQ ID NO: 21), AAEY-KAAAAAAAAAA (SEQ ID NO: 26), AAK-YEAAAAAAAAAA (SEQ ID NO: 28), AAKYAEAAAAAAAAA (SEQ ID NO: 29), AEYA-KAAAAAAAAAA (SEQ ID NO: 32), AEKAYAAAAAAAAAA (SEQ ID NO: 33), AYKAE-AAAAAAAAAA (SEQ ID NO: 35), and AKYAE-AAAAAAAAAA (SEQ ID NO: 36), the peptide having high affinity for an MHC class II protein. Yet another embodiment of the invention is an isolated peptide according to any of the preceding sequences in which the tyrosine (Y) has been substituted by a valine (F) or a phenylalanine (F).

Another embodiment of the invention provides an isolated peptide composition having an amino acid sequence capable of inhibiting immune response in a subject to an autoantigen, wherein a position in the amino acid sequence of the peptide that corresponds to an antigen binding pocket in a peptide binding groove of an MHC class II DR protein is identified as a particular amino acid. For example, an isolated peptide composition is provided wherein the autoantigen is associated with a condition selected from the group consisting of multiple sclerosis and arthritis. The MHC class II protein can be selected from the group consisting of an HLA-DR1 protein, an HLA-DR4 protein. In another embodiment, the MHC class II protein is MHC class II HLA-DR2. An embodiment of the invention provides an isolated peptide, wherein the amino acid residue in the position of the sequence that corresponds to the P1 pocket in the MHC class II peptide binding groove is selected from the group consisting of a tyrosine, a valine, and a phenylalanine. This embodiment further provides an isolated peptide composition wherein the amino acid residue in a first amino acid position of the sequence that corresponds to the P1 pocket in the MHC class II peptide binding groove is alanine. The embodiment further provides an isolated peptide composition, wherein the amino acid residue located eight residues beyond the first amino acid position of the sequence that corresponds to the P1 pocket in the MHC class II peptide binding groove is selected from the group consisting of lysine and alanine residues, and the amino acid residue that corresponds to the P1 pocket is selected from the group consisting of tyrosine, valine, and phenylalanine.

Another example of this invention provides a pharmaceutical preparation comprising a first peptide sequence and a second peptide sequence, wherein the composition is a mixture of first peptide sequence and the second peptide sequence, the first sequence having a lysine residue and the second sequence having an alanine residue at the amino acid position corresponding to eight residues beyond the amino acid corresponding to the P1 pocket in the MHC class II peptide binding groove.

The autoimmune disease is selected from the group consisting of: multiple sclerosis, myasthenia gravis, Hashimoto's disease, systemic lupus erythematosis, uveitis, Guillain-Barre' syndrome, Grave's disease, idiopathic myxedema, autoimmune oophoritis, chronic immune thrombocytopenic purpura, colitis, diabetes, psoriasis, pemphigus vulgaris, and rheumatoid arthritis. In particular, the therapeutic composition embodiment of the invention can be used to treat an autoimmune disease which is an arthritic condition. Further, the therapeutic composition embodiment of the invention can be used to treat an autoimmune disease which is a demyelinating disease. In yet another embodiment, the therapeutic composition embodiment of the invention can be used to treat an autoimmune disease which is an inflammatory disease. For example, an embodiment of the invention is a therapeutic composition to treat the autoimmune disease rheumatoid arthritis. In another example, an embodiment of the invention is a therapeutic composition to treat the autoimmune disease multiple sclerosis.

In another embodiment of the invention, a method is provided for obtaining an MHC class II amino acid binding motif sequence in a mixture of synthetic peptide heteropolymers having therapeutic activity in a subject, comprising the steps of: (a) binding the mixture of synthetic heteropolymers to MHC class II protein molecules to form a heteropolymer-MHC protein complexes; (b) removing by peptidase enzyme digestion the amino terminal amino acid residues of the heteropolymers protruding from the heteropolymer-MHC protein complex to align amino termini of the heteropolymers to the edge of the MHC protein complexes; and (c) eluting the aligned heteropolymers from the MHC protein by dissociating the complexes to release the amino terminal aligned heteropolymers having the binding motif. In this method an additional step (d) can comprise: determining the amino terminal sequence of the aligned heteropolymers to obtain the binding motif. Further, in this method an additional (e) can comprises: comparing the amino terminal sequence of the aligned heteropolymers to the amino acid sequence of the synthetic heteropolymer composition. In this method, the MHC class II protein is associated with an autoimmune disease, for example, the autoimmune disease is an arthritic condition or a demyelinating condition.

In another embodiment of this method, an additional step (e) can comprise: synthesizing a plurality of peptide preparations, each peptide preparation having an amino acid sequence of a binding motif. In a further aspect of this method, an additional step (f) comprises: determining the affinity of each of the synthesized peptides for the MHC class II protein.

DETAILED DESCRIPTION OF SPECIFIC EMBODIMENTS

Unless the context otherwise requires, as used in this description and in the following claims, the terms below shall have the meanings as set forth:

The term "autoimmune condition" means a disease state caused by an inappropriate immune response that is directed to a self-encoded entity which is known as an autoantigen.

The term "derivative" of an amino acid means a chemically related form of that amino acid having an additional substituent, for example, N-carboxyanhydride group, a γ-benzyl group, an ϵ,N-trifluoroacetyl group, or a halide group attached to an atom of the amino acid.

The term "analog" means a chemically related form of that amino acid having a different configuration, for example, an isomer, or a D-configuration rather than an L-configuration, or an organic molecule with the approximate size and shape of the amino acid, or an amino acid with modification to the atoms that are involved in the peptide bond, so as to be protease resistant when polymerized in a peptide or polypeptide.

The phrases "amino acid" and "amino acid sequence" can include one or more components which are amino acid derivatives and/or amino acid analogs comprising part or the entirety of the residues for any one or more of the 20 naturally occurring amino acids indicated by that sequence. For example in an amino acid sequence having one or more tyrosine residues, a portion of one or more of those residues can be substituted with homotyrosine. Further, an amino acid sequence having one or more non-peptide or peptidomimetic bonds between two adjacent residues, is included within this definition.

The term "hydrophobic" amino acid means aliphatic amino acids alanine (A, or ala), glycine (G, or gly), isoleucine (I, or ile), leucine (L, or leu), proline (P, or pro), and valine (V, or val), the terms in parentheses being the one letter and three letter standard code abbreviations for each amino acid, and aromatic amino acids tryptophan (W, or trp), phenylalanine (F, or phe), and tyrosine (Y, or tyr). These amino acids confer hydrophobicity as a function of the length of aliphatic and size of aromatic side chains, when found as residues within a protein.

The term "charged" amino acid means amino acids aspartic acid (D or asp), glutamic acid (E or glu), histidine (H or his), arginine (R or arg) and lysine (K or lys), which confer a positive (his, lys, and arg) or negative (asp, gly) charge at physiological values of pH in aqueous solutions on proteins containing these residues.

The term "anergy" means unresponsiveness of the immune system of a subject to an antigen.

The term "subject" as used herein indicates a mammal.

The term "arthritic condition" means at least one symptom of rheumatoid arthritis found in at least a single joint of a subject having the condition, for example in a shoulder, knee, hip or a digit of the subject. Examples of arthritic conditions include "polyarthritis", which is an arthritic condition that affects more than a single joint; "juvenile arthritis", an arthritic condition of a subject under the age of 21; and Felty's syndrome, which includes along with symptoms of rheumatoid arthritis (RA) also the symptoms of neutropenia, splenomegaly, weight loss, anemia, lymphadenopathy, and pigment spots on the skin.

The term "heterologous cell" means a cell for production of an MHC protein which is unrelated to a cell of a subject, i.e., the heterologous cell is not a cell of a mammal.

Preferably the heterologous cell is not from a warm blooded animal, even more preferably the heterologous cell is not from a vertebrate; in the most preferred embodiment the heterologous cell is an insect cell, or a cell of a microorganism such as a yeast cell.

The term "pharmaceutically acceptable carrier" includes any and all solvents, dispersion media, coatings, antimicrobials such as antibacterial and antifungal agents, isotonic and absorption delaying agents and the like that are physiologically compatible. Preferably, the carrier is suitable for intravenous, intramuscular, oral, intraperitoneal, transdermal, or subcutaneous administration, and the active compound can be coated in a material to protect it from inactivation by the action of acids or other adverse natural conditions.

This invention is directed to methods of use of a class of agents that can bind to specific MHC class II proteins. Such agent can bind to a class II protein, and thus inhibit and/or prevent the binding of an autoantigen involved in an autoimmune disease, or upon binding can induce anergy, so that there is no response of the immune system to the auto antigen.

The Class II MHC protein consists of two approximately equal-sized subunits, α and β, which are transmembrane proteins. A peptide-binding cleft, which is formed by protein features from the amino termini of both α and β subunits, is the site of presentation of the antigen to T cells. There are at least three types of Class II MHC molecules: HLA-DR, -DQ, and -DP, and there are numerous alleles of each type. The Class II MHC molecules are expressed predominantly on the surfaces of B lymphocytes and antigen presenting cells such as macrophages (Mengle-Gaw, L., *The Major Histocompat-*

Therapeutic Compositions in the Methods of the Invention

The methods of the invention include incorporation into a pharmaceutical composition suitable for administration to a subject an oligopeptide of defined sequence, for example, a peptide of length 9-20 residues, comprising the amino acid sequence glutamic acid-lysine-tyrosine (EKY).

A composition of the present invention can be administered by a variety of other methods known in the art as will be appreciated by the skilled artisan. The active compound can be prepared with carriers that will protect it against rapid release, such as a controlled release formulation, including implants, transdermal patches, microencapsulated delivery systems. Many methods for the preparation of such formulations are patented and are generally known to those skilled in the art. See, e.g., *Sustained and Controlled Release Drug Delivery Systems*, J. R. Robinson, Ed., Marcel Dekker, Inc., New York, 1978. Therapeutic compositions for delivery in a pharmaceutically acceptable carrier are sterile, and are preferably stable under the conditions of manufacture and storage. The composition can be formulated as a solution, microemulsion, liposome, or other ordered structure suitable to high drug concentration.

Dosage regimens can be adjusted to provide the optimum desired response (e.g., a therapeutic response). For example, a single bolus can be administered, several divided doses can be administered over time, or the dose can be proportionally reduced or increased as indicated by the exigencies of the disease situation.

In general, a preferred embodiment of the invention is to administer a suitable daily dose of a therapeutic composition that will be the lowest effective dose to produce a therapeutic effect, for example, mitigation of symptoms. The therapeutic compounds of the invention are preferably administered at a dose per subject per day of at least 2 mg, at least 5 mg, at least 10 mg or at least 20 mg as appropriate minimal starting dosages. In general, the compound of the effective dose of the composition of the invention can be administered in the range of 50 to 400 micrograms of the compound per kilogram of the subject per day.

A physician or veterinarian having ordinary skill in the art can readily determine and prescribe the effective dose of the pharmaceutical composition required. For example, the physician or veterinarian could start doses of the compound of the invention employed in the pharmaceutical composition at a level lower than that required in order to achieve the desired therapeutic effect, and increase the dosage with time until the desired effect is achieved.

In another preferred embodiment, the pharmaceutical composition includes also an additional therapeutic agent. Thus in a method of the invention the pharmaceutical composition can be administered as part of a combination therapy, i.e. in combination with an additional agent or agents. Examples of materials that can be used as combination therapeutics with the peptides herein for treatment of autoimmune disease and arthritic conditions as additional therapeutic agents include: an antibody or an antibody fragment that can bind specifically to an inflammatory molecule or an unwanted cytokine such as interleukin-6, interleukin-8, granulocyte macrophage colony stimulating factor, and tumor necrosis factor-α; an enzyme inhibitor which can be a protein, such as $\alpha_1$-antitrypsin, or aprotinin; an enzyme inhibitor which can be a cyclooxygenase inhibitor; an engineered binding protein, for example, an engineered protein that is a protease inhibitor such an engineered inhibitor of kallikrein; an antibacterial agent, which can be an antibiotic such as amoxicillin, rifampicin, erythromycin; an antiviral agent, which can be a low molecular weight chemical, such as acyclovir; a steroid, for example a corticosteroid, or a sex steroid such as progesterone; a non-steroidal anti-inflammatory agent such as aspirin, ibuprofen, or acetaminophen; an anti-cancer agent such as methotrexate or adriamycin; or a cytokine. An additional therapeutic agent can be a cytokine, which as used herein includes without limitation agents which are naturally occurring proteins or variants and which function as growth factors, lymphokines, interferons, tumor necrosis factors, angiogenic or antiangiogenic factors, erythropoietins, thrombopoietins, interleukins, maturation factors, chemotactic proteins, or the like. Preferred combination therapeutic agents to be used with the composition of the invention and which are cytokines include interleukin-4 and interleukin-10. A therapeutic agent to be used with the composition of the invention can be an engineered binding protein, known to one of skill in the art of remodeling a protein that is covalently attached to a virion coat protein by virtue of genetic fusion (Ladner, R. et al., U.S. Pat. No. 5,233,409; Ladner, R. et al., U.S. Pat. No. 5,403,484), and can be made according to methods known in the art. A protein that binds any of a variety of other targets can be engineered and used in the present invention as a therapeutic agent in combination with a peptide of the invention.

An improvement in the symptoms as a result of such administration is noted by a reduction in edema of one or more joints, by a reduction in inflammation in one or more joints, or by an increase in mobility in one or more joints. A therapeutically effective dosage preferably reduces joint inflammation and edema and improves mobility by at least about 20%, more preferably by at least about 40%, even more preferably by at least about 60%, and even still more preferably by at least about 80%, relative to untreated subjects.

The therapeutic compounds of the invention can be used to treat symptoms of an autoimmune disease, a class of disorder which include Hashimoto's thyroiditis; idiopathic myxedema, a severe hypothyroidism; multiple sclerosis, a demyelinating disease marked by patches or hardened tissue in the brain or the spinal cord; myasthenia gravis which is a disease having progressive weakness of muscles caused by autoimmune attack on acetyicholine receptors at neuromuscular junctions; Guillain-Barre syndrome, a polyneuritis; systemic lupus erythematosis; uveitis; autoimmune oophoritis; chronic immune thrombocytopenic purpura; colitis; diabetes; Grave's disease, which is a form of hypothyroidism; psoriasis; pemphigus vulgaris; and rheumatoid arthritis (RA).

Another embodiment of the invention is a kit for assaying the binding of an analyte to an MHC protein. This embodiment provides: a water-soluble MHC protein which has been recombinantly produced in a non-mammalian cell; a reaction chamber for containing the analyte and the MHC protein; and means for detecting binding of the analyte to the MHC protein. In a preferred embodiment, the MHC protein is produced in an invertebrate or a microbial cell, such as an insect cell or a yeast cell, and so is devoid of bound peptide in the antigen cleft, i.e., the MHC protein is "empty." Means for detecting binding of the analyte to the MHC protein can be radioactive, fluorimetric, chemiluminescent, or colorimetric means known to one of ordinary skill in the art. In a preferred embodiment of the kit, the MHC protein is a class II MHC HLA-DR1 or -DR4 protein. Further, the kit can include also an autoantigenic peptide, such as a CII peptide, or a peptide derived from myelin basic protein, myelin oligodendrite protein, or a peptide from some other protein implicated in an autoimmune disease.

Previous findings suggested that the activity of YEAK (Cop 1) in EAE and MS involves binding to class II MHC molecules within the peptide binding groove, resulting in suppression of autoimmune T cell responses that can be related to MS (Teitelbaum, D., et al., 1988, *Proc. Natl. Acad. Sci.* USA 85:9724; Teitelbaum, D., et al., 1992, *Proc. Natl. Acad. Sci.* USA 89: 137; Fridkis-Hareli, M. et al. 1998, *J. Immunol.* 160:4386, the contents of which are hereby incorporated by reference).

The recombinant empty HLA-DR1 and -DR4 molecules that were here used in assays yielded data for binding that is free from interference due to previously bound endogenous peptides. In contrast, for prior analyses of binding to human HLA-DR1 and DR4 molecules, only 10-20% of the receptor proteins had been available for binding of exogenously supplied peptide (see, for example, Hammer, J. et al., 1993, *Cell* 74:197-203), resulting in determinations of binding affinities for the heteropolymers that in the present invention are different and more accurate compared to those reports.

YEAK binds with high affinity and in a peptide-specific manner to purified MS-associated HLA-DR2 (DRB1*1501) and rheumatoid arthritis (RA)-associated HLA-DR1 (DRBI*0101) or HLA-DR4 (DRB1*0401) molecules. Since YEAK is a mixture of random polypeptides, it may contain different sequences that bind to different HLA proteins; in this case only a fraction out of the whole mixture would be an "active component." Alternatively, the whole mixture may be competent, i.e. all polypeptides binding to any HLA-DR molecule.

Example 1 shows methods for isolating and purifying a fraction of YEAK that bound to recombinant "empty" HLA-DR1, -DR2 and -DR4 molecules, produced so as to have minimal interference from endogenous human peptides. Example 2 shows the distribution of amino acid residues in the fraction of YEAK molecules that bound to the HLA-DR protein molecules. The amino acid composition, HPLC profiles and pool sequence, and immunological recognition of the fraction of the heteropolymer bound to MHC class II protein groove were determined.

Since the average length of the YEAK polypeptides used was 75-80 amino acids, the amino acid sequences comparable to "epitopes" lying in the groove of HLA-DR molecules were likely to be found internally within the polypeptide chains. The presence of the contiguous amino ends of the polymer that were protruding from the complexes could obscure the sequences of binding motifs to be obtained by microchemical methods of sequence analysis applied directly to the bound YEAK fraction. Because of this consideration, amino-terminal aminopeptidase treatment in Example 3 of the protruding ends of YEAK polypeptides was employed to access the internal regions and obtain the binding motif sequences. Since the aminopeptidase trims amino-terminal ends of peptides that protrude from the class II MHC proteins, epitopes that were bound to the groove of the proteins can be protected from aminopeptidase proteolysis.

In Example 4, various 15-mer amino acid peptides were synthesized to resemble sequences of the MHC class II DR-i and -4 binding motifs obtained from the binding motif sequences found in Example 3. The peptides were tested in Example 5 to determine if they differentially inhibited binding of disease-associated HLA-DR1 (DRB 1*0101) or HLA-DR4 (DRB1*0401) protein molecules to YEAK and to the immunodominant epitope of collagen type II (CII) 261-273, a candidate autoantigen in rheumatoid arthritis (RA). Peptide sequences in Example 6 were further tested to obtain those with ability to inhibit significantly the response of HLA-DR1- and -DR4-restricted T cell clones to the CII epitope 261-273 in cell culture in vivo. The findings that certain peptides bind with high specificity and affinity and inhibit T cell activation in Examples 5 and 6 indicate utility of certain of the 15-mer amino acid peptide compounds as therapeutic agents in treatment of autoimmune diseases such as RA and MS.

EXAMPLES

Methods for Preparing Heteropolymers and Protein Reagents

Synthesis of Heteropolymers and Peptides

Heteropolymer YEAK (Cop 1) was prepared as described by polymerization of the N-carboxyanhydrides of L-alanine, γ-benzyl-L-glutamate, ϵ,N-trifluoroacetyl-L-lysine, and L-tyrosine (Teitelbaum, D., et al., 1971, *Eur. J. Immunol.* 1:242). The end product is a mixture of acetate salts of random polypeptides. Heteropolymers EAK, batch SD-1689, MW 8,850; YEA, batch SD-1690, MW 7,600; YAK, batch SD-1691, MW 20,000; and YEK, batch SD-1697, MW 11,050 were synthesized also by polymerization of the N-carboxyanhydride substrates (Teva Pharmaceuticals, Inc., Petach Tiqva, Israel; Fridkis-Hareli, M. et al. 1998, *J. Immunol.* 160:4386, the contents of which are hereby incorporated herein by reference). Heteropolymers can be synthesized also by solid state techniques. Natural peptide sequences influenza hemagglutinin HA peptide 306-318 having the sequence PKYVKQNTLKLAT (SEQ ID NO: 1) and collagen II (CII) peptide 261-273 having the sequence AGFKGEQGPKGEP (SEQ ID NO: 2) were synthesized using solid phase techniques (Barany, G. et al., 1979, *Academic Press*, New York. p. 1) on an Applied Biosystems Peptide Synthesizer (Foster City, Calif.) and purified by reverse-phase HPLC. For these and other methods used throughout these examples, see also Fridkis-Hareli et al. 1998, Proc. Natl. Acad. Sci. U.S. 95:12528-12531, Fridkis-Hareli et al. 1999 J. Immunol. 162: 4697-4704, and Fridkis-Hareli et al. 1999, Internat. Immunol. 11:635-641, the contents of each of which are herein incorporated by reference hereby.

The one letter and the three letter amino acid codes (and the amino acid that each represents) are as follows: A means ala (alanine); C means cys (cysteine); D means asp (aspartic acid); E means glu (glutamic acid); F means phe (phenylalanine); G means gly (glycine); H means his (histidine); I means ile (isoleucine); K means lys (lysine); L means leu (leucine); M means met (methionine); N means asn (asparagine); P means pro (proline); Q means gln (glutamine); R means arg (arginine); S means ser (serine); T means thr (threonine); V means val (valine); W means trp (tryptophan); and Y means tyr (tyrosine).

Protein Expression and Purification

Recombinant HLA-DR1 and -DR4 molecules were expressed in Drosophila S2 cells as described (Stern, L. et al. 1992, Cell 68:465; Dessen, A. et al. 1997, *Immunity* 7:473). Cells were grown in roller bottles at 26° C. in Excell 401 medium (Sigma, St. Louis, Mo.) supplemented with 0-5% fetal bovine serum (Sigma). Cells were induced by addition of $CUSO_4$ to 1 mM final concentration, and cells were incubated an additional 4-5 days. Immunoaffinity purification of recombinant HLA-DR1 and DR4 was performed as previously reported (Stern, L. et al. 1992, Cell 68:465; Dessen, A. et al. 1997, *Immunity* 7:473). Supernatant from harvested cells was sequentially passed through Protein A, Protein G and Protein A-LB3.1 columns, followed by elution of the bound HLA-DR with 50 mM 3-cyclohexylamino-1-propane sulfonic acid (CAPS), pH 11.5, and neutralized with 200 mM phosphate (pH 6.0). The eluate was concentrated on a Centriprep 10 membrane (Amicon). Protein concentrations were determined by bicinchoninic acid assay (Pierce Chemical Co.).

Class II-Peptide-Binding Assays

The solutions used in this assay are described in Fridkis-Hareli, M. et al. 1998, J. Immunol. 160:4386. Assays were performed in 96-well microtiter immunoassay plates (PRO-BIND™, Falcon) which were coated with affinity-purified LB3.1 monoclonal antibodies, 100 µl of 1.0 µg/well in PBS (150 mM sodium chloride, 7.5 mM sodium phosphate dibasic, 2.5 mM sodium phosphate monobasic, pH 7.2) by incubation for 18 hrs at 4° C. The wells were then blocked with TBS (137 mM sodium chloride, 25 mM TRIS pH 8.0, 2.7 mM potassium chloride) containing 3% BSA (bovine serum albumin) for 1 hr at 37° C. and washed three times with TTBS (TBS with 0.05% Tween-20). Before sample addition, 50 µl of TBS containing 1% BSA was added to each well.

Water-soluble HLA-DR1 molecules were recombinantly produced in a heterologous host cell, for example, insect cells infected with recombinant baculoviruses (Stern, L. J. et al, 1992, Cell 68:465), specifically in Drosophila S2 cells as described supra. Binding analysis was performed by coincubating biotinylated YEAK (final concentration, 1.5 µM) in 50 µl of the binding buffer in duplicate with varying concentrations of unlabeled inhibitors (CII 261-273 or HA 306-318), and with recombinant water soluble DR molecules (0.5 µg) for 40 hr at 37° C. at pH 5.0.

Detection of Peptide-Class II Complexes

Bound peptide-biotin was detected using streptavidin-conjugated alkaline phosphatase as follows. Plates were washed three times with TTBS and incubated with 100 µl of streptavidin-conjugated alkaline phosphatase (1:3000, BioRad, Richmond, Va.) for 1 hr at 37° C., followed by addition of p-nitrophenyl phosphate in triethanolamine buffer (BioRad). The absorbance at 410 nm was monitored by a microplate reader (model MR4000, Dynatech, Chantilly, Va.).

T Cell Hybridomas and Antigen Presentation Assays

The following mouse T cell hybridomas specific for CII were used: DR1-restricted 3.19 and 19.3 clones (Rosloniec, B. F., et al., 1997, J. Exp. Med. 185: 1113-1122.), and DR4-restricted 3838 and D3 clones (Andersson, E. C., et al., 1998, Proc. Natl. Acad. Sc. USA). APC were L57.23 (L cells transfected with DR1 (Rosloniec, E. F., et al., 1997, J. Exp. Med. 185: 1113-1122)), L cells transfected with DR4, and Press cells (DRB1*04O1/DRB4*0101). T cell stimulation experiments were performed in 96-well microtiter plates in a total volume of 0.2 ml. Irradiated (3000 rad) APC ($2.5 \times 10^4$/well) were coincubated with CII 261-273 (40 µg/ml) and varying concentrations of heteropolymers or peptides for 2 hr at 37° C., then T cells ($5 \times 10^4$/well) were added and incubations were continued for 24 hr at 37° C. Supernatants (30 µl) were removed and incubated with IL-2-dependent CTL-L ($5 \times 10^4$/well) for 12 hr, followed by labeling with $^3$H-thymidine (1 µCi/well) for 12 hr. Plates were harvested and the radioactivity was monitored using a 1450 microbeta Plus liquid scintillation counter (Wallac, Gaithersburg, Md.).

Example 1

Methods for Preparation and Quantitation of YEAK Bound to HLA-DR1 -DR2 and -DR4 Molecules YEAK was incubated with water-soluble HLA-DR1, -DR2 or -DR4 molecules at the molar ratio of 1:1 for 40 hr at 37° C. These recombinant "empty" HLA-DR molecules can be stably assembled in the presence of exogenously added antigen, and YEAK can function to promote stabilization and with no interference from endogenous peptides (Fridkis-Hareli, M. et al. 1998. J. Immunol. 160:4386). Unbound YEAK was separated from bound YEAK by Centricon ultrafiltration. Bound YEAK was then extracted from the HLA-DR complex by acid treatment (Chicz, R. et al. 1993. J. Exp. Med. 178:27) and subjected to amino acid analysis.

For HPLC separation and microsequencing after elution, approximately 5-10% of the YEAK mixtures were fractionated by microbore HPLC using a Zorbax $C_{18}$ 1.0 mm reverse-phase column on a Hewlett-Packard 1090 HPLC with 1040 diode array detector. At a flow rate of 54 µl/min, YEAK was eluted with a gradient of 0.055% trifluoroacetic acid (TFA) in acetonitrile (0% at 0 to 10 mm, 33% at 73 mm and 60% at 105 min). Strategies for peak election, reverse phase separation and Edman microsequencing were performed as in Chicz, R. et al. 1993. J. Exp. Med. 178:27, and Lane, W. et al. 1991. J. Prot. Chem 10:151.

To further characterize the bound fraction of YEAK by means of hydrophobicity and size, samples were separated on RP-HPLC using an acetonitrile gradient. Untreated YEAK showed a very broad peak with several smaller peaks, which spread between approximately 40 and 75 mm elution time. This elution profile is characteristic of a mixture of random polypeptides and resembles HPLC separations of other batches of YEAK. Similar profiles were obtained when YEAK was eluted from HLA-DR1, -DR2 or -DR4 molecules, indicating that the bound fraction is similar to the whole original YEAK mixture in its chemical properties.

Example 2

Analysis of YEAK Bound to HLA-DR1, -DR2, and -DR4 Molecules

At least 95% of the added YEAK heteropolymer molecules was observed in the fraction that was bound to isolated HLA-DR1 and HLA-DR4, and 80% was bound to HLA-DR2 proteins. YEAK that was eluted from the complexes with HLA-DR1, -DR2 and -DR4 molecules showed ratios of the component amino acids YEAK similar to that of control untreated YEAK. These results indicate that the bound fraction of YEAK reflected the amino acid composition of the whole mixture and that the YEAK population exhibited little or no preferential binding to different HLA-DR proteins. When YEAK was incubated with an excess of each of HLA-DR1, -DR2 and -DR4 molecules that had been purified from human homozygous EBV-transformed B cell lines, and the complexes were further fractionated by passage through a size-exclusion column, the distribution of eluted material showed that nearly all of the YEAK was found in the fractions corresponding to the high molecular weight complexes, with less than 10% at the lower molecular weight position of control YEAK, for each of the HLA-DR molecules.

To analyze the sequence of YEAK that bound to each of HLA-DR1, -DR2 and -DR4 molecules, HPLC fractions obtained in Example 5 were pooled within the areas of elution, and pooled fractions were submitted to automated Edman degradation on a Hewlett-Packard G1005A (Palo Alto, Calif.) protein sequencer using the manufacturer's Routine 3.5.

For each of the HLA-DR proteins, the results showed that the four amino acid components of YEAK bound to protein were randomly distributed within the sequence according to the input molar ratios of YEAK. Amino acid alanine (A) was found at significantly higher levels compared to E, Y and K, as expected from the initially higher molar ratio of A in YEAK. There was no sequence specificity or preferential positioning of any of the amino acids of YEAK, indicating that the bound fraction was also random and similar to the entire unfractionated YEAK.

Anti-YEAK polyclonal antibodies were used to determine whether fractions of YEAK eluted from each of the HLA-DR molecules contained the epitopes found in control untreated YEAK. The cross reactivity between YEAK and various YEAK fractions was detected by direct ELISA assay using biotinylated anti-YEAK polyclonal antibodies. YEAK or fractions were diluted to 0.4 µg/ml and 2.0 µg/ml and 100 µl/well was plated in duplicate on a 96-well microtiter immunoassay plate (PRO-BIND™, Falcon, Lincoln Park, N.J.), incubated for 1 hr at 37° C. and washed three times with TBS containing 0.05% Tween-20. The wells were then blocked with TBS containing 3% BSA, followed by addition of biotinylated anti-YEAK antibodies (at a dilution of 1:5000, 100 µl/well). Antibody-ligand complexes were detected using streptavidin-conjugated alkaline phosphatase (at a dilution of 1:3000, BioRad) and p-nitrophenyl phosphate in triethanolamine buffer (BioRad; Hercules, Calif.). The absorbance at 410 nm was monitored by a microplate reader (Dynatech MR4000).

The antibody binding assays showed that all the fractions were similarly recognized by anti-YEAK antibodies, suggesting that these bound heteropolymer fractions shared similar or identical epitopes with each other and with control YEAK.

Example 3

Characterization of Binding Motifs of YEAK by Removal of Protruding Amino Termini of YEAK Bound to HLA-DR1, -DR2 or -DR4 Molecules with Aminopeptidase I The sequences of the first 20 to 25 N-termini amino acids observed in Example 6 represent the sequences that protrude from beyond the HLA-DR molecules, so are not a source of information regarding the actual binding motif(s) of YEAK bound within the functional epitope-specific groove. To obtain the amino acid sequence of the portion of the YEAK molecule bound within the MHC class II protein and so protected by this protein, YEAK (1 mM) was initially incubated with each of the HLA-DR molecules (100 µM) in a volume of 10 µl at the molar ratio of 10 YEAK:1 HLA-DR, in PBS for 40 hours at 37° C. Aminopeptidase I, a metalloprotein isolated from *Streptomyces griseus* (Spungin A. et al. 1989. *J. Biochem.* 183:471; available from Sigma Chemicals, St. Louis, Mo.), was added to the reaction in a volume of 2 µl containing 2 units for the last 18 hr of incubation, in order to remove amino-terminal ends of YEAK polypeptides protruding from the HLA-DR molecules, and to digest remaining unbound YEAK (Mouritsen, S. et al. 1992. *J. Immunol.* 148: 1987; Larsen, S. L. et al. 1996. *J. Exp. Med.* 184:183). Subsequent digestions of heteropolymer with aminopeptidase was performed in volumes scaled up by a factor of twenty-forty fold, for example, 300 µl of heteropolymer digested with 60 µl of aminopeptidase. Samples were spin-concentrated to a final volume of approximately 100 µl using Centricon 10 ultrafiltration devices.

The YEAK-HLA-DR complexes and the unbound YEAK were analyzed by SDS-PAGE. SDS-PAGE was carried out with the NOVEX mini cell electrophoresis system. Separation gel was 10% in acrylamide and stacking gel was 5%. HLA-DR1-YEAK complexes were run under nonreducing conditions for 1 hr at 200 V, stained with Coomassie Brilliant Blue, fixed for 3 hr in 10% methanol/10% acetic acid and dried on Cellophane paper (BioRad) at 25° C. The YEAK-HLA-DR complexes were found to be resistant to SDS-induced dissociation, forming higher molecular weight complexes with HLA-DR1 αβ heterodimers, and were observed as numerous bands on the polyacrylamide gel with molecular weights greater than the molecular weight protein standard of 50 kD, showing that the YEAK-DR complexes were protected. Aminopeptidase I treatment resulted in unbound YEAK appearing as a smear in the lower part of the gel, showing that it was completely digested by the enzyme.

To obtain the sequence of the binding motifs, fractions containing the peaks of protected YEAK were selected in the region between approximately 40 and 75 mm elution time for each class of HLA-DR complex. Bound YEAK absent the protruding N-termini was eluted from HLA-DR by addition of acetic acid (10%) and incubation at 70° C. for 15 mm, followed by ultrafiltration and vacuum concentration in a SPEEDVAC (vacuum centrifugation instrument; Savant Instruments, Farmingdale, N.Y.; Fridkis-Hareli, M. et al. 1995. *Cell. immunol.* 163:229). The sequence data (Table 2) show that for peptides bound to HLA-DR1, significantly higher levels of the E residue were found at the first and second cycles, higher levels of K residue were found at the second and third cycles, and higher levels of Y residue were found at the third to fifth cycle (presumably at the position corresponding approximately to the P1 of the bound peptide site within the MHC class II groove). The amino acid residue obtained from position 3 from the Edman degradation method corresponds to the P1 anchor position of the MHC class II peptide binding groove, since in the structure of the HA 306-318 complex with HLA-DR1, the P-2 amino acid residue is at the flush end of the groove and the P1 position is the third amino acid, that is, Y308, in a deep pocket (Stern, L. et al., *Nature (Lond.)* 368:215). These data are in contrast to the random patterns of the sequences found in untreated YEAK, which showed no sequence specificity or preferential positioning within the MHC class II groove of any of the four amino acids that comprise YEAK.

For HLA-DR2, both Y and A residue levels were enriched at cycle 3 (Table 1). No sequence specificity or preferential positioning was observed for positions corresponding to anchor positions following P1 (at positions in the sequence that correspond to the P4, P6 or P9 of HLA-DR1 or -DR4; P4, P7 of DR2b molecules). In all the samples the levels of A were higher than those of E, Y and K, a finding which was expected and corresponds to the higher molar ratio of A in YEAK. For each of the HLA-DR-1 and -4 molecules, Y was found at the position corresponding to the first anchor position (the third residue in the sequence analysis), followed by A in the positions corresponding to the subsequent pockets. In the YEAK bound to HLA-DR2 also, Y was enriched at the position corresponding to P1. At the first cycle position corresponding to the P-2 position, E was enriched, and at the next adjacent position corresponding to P-1, K was enriched. These residues can contribute to the stable interactions of YEAK with the HLA-DR molecules and the interaction of this complex with the T cell receptor (TCR).

These results indicate that YEAK contains class II MHC binding motifs. Without being bound by any particular theory, it is shown by these data that YEAK, bound to the antigen groove of HLA-DR molecules, can act either as a blocking peptide or as an antagonist or partial agonist, resulting in suppression of autoimmune T cell responses or energy, or both. The binding motif sequences are useful for mapping the T cell epitopes, and for design of novel agents for the treatment of autoimmune diseases, such as MS and RA in humans.

Example 4

Synthesis of Peptides Having Binding Motifs for HLA-DR1 and -DR4 Molecules

Examples above show that the YEAK heteropolymer bound to purified human HLA-DR molecules within the peptide binding groove and inhibited the binding of HA 306-318 peptide, a high affinity epitope of influenza virus, to both HLA-DR1 (DRB1*0101) and -DR4 (DRB1*0401) molecules. The fraction of YEAK that bound to the protein was isolated from complexes with recombinant "empty" HLA-DR molecules produced in insect cells, and binding motifs were resolved by aminopeptidase I treatment of the YEAK that bound to the complex in the major groove of HLA-DR1 or -DR4 molecules. Subsequent pool sequencing of eluted peptides showed increased in levels of E at the first and second cycles, of K at the second and third cycles, and of Y (at P1 of the bound peptide) at the third to fifth cycle of the amino acid residues, regardless of the HLA-DR molecule employed.

TABLE 1

Binding motif sequences of YEAK bound to HLA-DR 1, -DR2 and -DR4 molecules

| HLA-DLR | | relative amino acid positions | | | | | |
|---|---|---|---|---|---|---|---|
| | | -2 | -1 | 1 | 4 | 6 | 7 | 9 |
| DRBI*0101 | DR-1 | E | K | Y | A | A | A | A |
| DRBI*0401 | DR-4 | F | K | Y | A | A | A | A |
| DRBI*1501 | DR-2 | E | K | Y,A | A | A | A | A |

In this Example, peptides of defined sequence and 15 residue length were synthesized using the sequences of the binding motifs summarized in Table 1. These peptides were analyzed in the Examples below for affinity and specificity of binding to MHC class II HLA DR protein molecules and for ability to inhibit binding of competitor molecules and ability to inhibit T cell responses, functional properties appropriate to a novel therapeutic composition for an autoimmune disease.

Peptides shown in Table 2 were synthesized using solid phase techniques (Barany, G. et al., 1979. *The Peptides*, B. Gross et al., eds. (New York, N.Y.: Academic Press) on an Applied Biosystems Peptide Synthesizer, and were purified by reversed-phase HPLC. Peptide sequences included HA 306-318, PKYVKQNTLKLAT (SEQ ID NO: 1), MW 1718; CII 261-273, AGFKGEQGPKGEP (SEQ ID NO: 2), MW 1516; and HA 306-318 bracketed by alanines at N- and C-terminals, APKYVKQNTLKLATA (SEQ ID NO: 4). For comparison, the CII 261-273 peptide, bracketed by alanines at N- and C-terminals, AGFKGEQGPKGEP (SEQ ID NO: 2), can be synthesized. Peptides were also synthesized on a 1 μmole scale using the Multipin Peptide Synthesis System (Chiron Technologies, Raleigh, N.C.). Peptides were synthesized as 15-mers with free amino groups at the N-terminus and free carboxyl groups at the C-terminus, and with biotin linked to the N-terminus by the spacer SGSG and having a free carboxyl group at the C-terminus. Peptide synthesis was monitored by including two standard peptide sequences as controls, which were subjected to HPLC and mass spectroscopy analysis. HA 306-318 peptide was also used as a positive control for binding experiments. Pin peptides were lyophilized and resuspended at a concentration of 2 mg/ml in dimethyl sulfoxide (DMSO). Under these conditions, the majority of peptides were completely solubilized. Biotinylation was performed with excess N-hydroxysuccinimide biotin (Sigma, St. Louis, Mo.) in DMSO as described (Fridkis-Hareli et al., 1994. *Proc. Natl. Acad. Sci.*, U.S.A. 91:4872-4876). Unreacted biotin was removed by dialysis (SpectrafPor® membrane MWCO 500, Spectrum Medical Industries, Houston, Tex.).

The 15-mer peptides (SEQ ID NOs: 5-36; see Table 2) synthesized based on the motifs for binding of YEAK to the groove of HLA-DR1 and -DR4 molecules contained various combinations of E, K and A at the N-terminus for most of the peptides, followed by Y at the position corresponding to P1 (shown in bold), and then A in the subsequent binding pockets. The sequences fall into three different groups according to these positions in the consensus (Table 2). Peptides in group I had K at the position corresponding to P8 and Y at the position corresponding to P1 (in bold in Table 2). A reference peptide in this set with lysine (K) at the position corresponding to P8 to increase solubility and alanine (A) at all other residues had previously been synthesized (SEQ ID NO: 5; Jardetzky, T. S., et al. 1990. *EMBO J.* 9, 1797-1803). Peptides in group II had Y at the position corresponding to P1, however had A at the position corresponding to P8. Peptides in group III had amino acid tyrosine (Y) shifted one or two residues with respect to that in HA 306-318 peptide. Peptides in all groups contained one or more glutamic acid (E) and/or lysine (K) residues, as was observed in the binding motifs supra, and to enhance solubility. Both N-terminal biotinylated and unlabeled sets of peptides were synthesized for these studies.

TABLE 2

Groups of synthetic peptides and consensus positions.

| group | SEQ ID NO | Peptide sequence | amino acid consensus positions |
|---|---|---|---|
| Control | 4 | APKYVKQNTLKLATA | A(HA 306-318)A |
| I. | 5 | AAAYAAAAAKAAAA | P1Y, P8K |
| | 6 | AEKYAAAAAKAAAA | |
| | 7 | AKEYAAAAAKAAAA | |
| | 8 | AKKYAAAAAKAAAA | |
| | 9 | AEAYAAAAAKAAAA | |
| | 10 | KEAYAAAAAKAAAA | |
| | 11 | AEEYAAAAAKAAAA | |
| | 12 | AAEYAAAAAKAAAA | |

TABLE 2-continued

Groups of synthetic peptides and consensus positions.

| group | SEQ ID NO | Peptide sequence | amino acid consensus positions |
|---|---|---|---|
|  | 13 | EKAYAAAAAAKAAAA |  |
|  | 14 | AAKYEAAAAAKAAAA |  |
|  | 15 | AAKYAEAAAAKAAAA |  |
|  | 16 | EAAYAAAAAAKAAAA |  |
|  | 17 | EKKYAAAAAAKAAAA |  |
|  | 18 | EAKYAAAAAAKAAAA |  |
| II. | 19 | AEKYAAAAAAAAAAA | P1Y, P8A |
|  | 20 | AKEYAAAAAAAAAAA |  |
|  | 21 | AKKYEAAAAAAAAAA |  |
|  | 22 | AKKYAEAAAAAAAAA |  |
|  | 23 | AEAYKAAAAAAAAAA |  |
|  | 24 | KEAYAAAAAAAAAAA |  |
|  | 25 | AEEYKAAAAAAAAAA |  |
|  | 26 | AAEYKAAAAAAAAAA |  |
|  | 27 | EKAYAAAAAAAAAAA |  |
|  | 28 | AAKYEAAAAAAAAAA |  |
|  | 29 | AAKYAEAAAAAAAAA |  |
|  | 30 | EKKYAAAAAAAAAAA |  |
|  | 31 | EAKYAAAAAAAAAAA |  |
| III. | 32 | AEYAKAAAAAAAAAA | P1A, P8A |
|  | 33 | AEKYAAAAAAAAAAA |  |
|  | 34 | EKYAAAAAAAAAAAA |  |
|  | 35 | AYKAEAAAAAAAAAA |  |
|  | 36 | AKYAEAAAAAAAAAA |  |

Example 5

Inhibition of YEAK and Antigen Binding to HLA-DR Molecules by the Synthetic 15-Mer Peptides To examine whether the synthetic peptides can compete successfully for binding to HLA-DR1 and -DR4 with YEAK or with the high affinity HA 306-318 peptide, competitive binding assays were carried out with both biotinylated YEAK or HA 306-318 (bracketed by alanines) and unlabeled inhibitors (YEAK and the synthetic 15-mer peptides). Kinetic studies indicated that biotinylated YEAK inhibited binding of unlabeled YEAK and of HA 306-318 (peptide SEQ ID NO: 4) to recombinant HLA-DR1 better than of peptides in groups I-III. However, several peptides containing K at the position corresponding to P8 (group I) were better inhibitors than peptides that were similar but having A at the position corresponding to P8 (from groups II and III of Table 2). In contrast, the binding of biotinylated YEAK to HLA-DR4 molecules was efficiently inhibited by many of the peptides in groups 1-111, but the binding of biotinylated HA 306-318 to HLA-DR4 was better inhibited by YEAK than by HA 306-318 or by the 15-mer peptides.

To further characterize the relative affinity of the synthetic 15-mer peptides to compete with each of YEAK, HA 306-318 or CII 261-273 for binding to HLA-DR1, -DR2 and -DR4 molecules, competitive binding assays were carried out with biotinylated Multipin peptides and the three unlabeled inhibitors. The binding of the majority of the peptides in groups I-III to both HLA-DR1 and HLA-DR4 was inhibited by unlabeled YEAK, HA 306-318 (SEQ ID NO: 4) or CII 261-273 (SEQ ID NO: 2), however, less efficiently than the binding of HA 306-318 (SEQ ID NO: 4). Some of the peptides however showed higher affinity for the HLA proteins than did YEAK, HA306-318, or CII 261-273.

TABLE 3

Affinity of selected YEAK-related peptides for HLA-DR1 (DRB1*0101) molecules determined by competition with biotinylated competitors HA306-318 and YEAK (µM)

| SEQ ID NO | peptide sequence | HA 306-318 | YEAK |
|---|---|---|---|
| 4 | APKYVKQNTLKLATA | 13.0 | 3.3 |
| 7 | AKEYAAAAAAKAAAA | 19.0 |  |
| 12 | AAEYAAAAAAKAAAA | 47.0 |  |
| 15 | AAKYAEAAAAKAAAA | 42.0 | 16.0 |
| 18 | EAKYAAAAAAKAAAA | 33.0 |  |
|  | YEAK | 10.0 | 8.0 |

All peptides were further tested for ability to inhibit CII-specific T cell responses.

Example 6

Inhibition of HLA-DR1 and -DR4-Restricted CII-Specific T Cell Responses by the 15-Mer Synthetic Peptides To determine whether the synthetic peptides could also inhibit presentation of the CII 261-273 peptide to autoreactive T cells, complexes of APC and peptides were tested with CII-specific T cell hybridomas restricted to HLA-DR1 (3.19 and 19.3) and HLA-DR4 (3838 and D3). Irradiated APC were incubated with CII 261-273 and of each of the relevant peptides for 2 hrs, T cells were added and the incubation continued for 24 hrs, and supernatants were tested to determine quantities of IL-2 secretion by these hybridomas as a measure of T cell activation.

Peptides SEQ ID NOs: 15 and 26 were observed to be the most potent inhibitors of HLA-DR1-restricted T cells, using L fibroblasts transfected with HLA-DR1 as APC for the CII peptide. Peptides 15, 20, 26 and 27 inhibited responses to 19.3 T cells essentially 100%, to levels of inhibition greater than observed with HA 306-318. For 3.19 cells, inhibition by peptide #26 was equivalent to that of HA 306-318. YEAK had little effect on this CII-specific T cell response (inhibition less than 20%). HA 306-318 (peptide SEQ ID NO: 4) inhibited both DR1 3.19 and 19.3 T cell clones very efficiently (over 95% and 98% for 19.3 and 3.19 cells, respectively). These data show that peptides of SEQ ID NO: 15, 20, 26, and 27 were as good or better inhibitors of T cell response than the reference influenza virus hemagglutinin peptide HA 306-318.

For HLA-DR4-restricted T cells, using L fibroblasts transfected with HLA-DR4 as APC, the following pattern of activity was obtained: peptides SEQ ID NOs: 6, 11, 16, 17, 22, 23, 27, 28 and 33 were good inhibitors of the DR4 3838 T cell clone, whereas the D3 clone was inhibited best by peptides SEQ ID NOs: 8, 15, 16, 18 and 27. These peptides produced levels of inhibition of over 80% for the D3 and 3838 cells. YEAK had only a minimal effect on the CII-specific T cell response, consistently giving less than 20% inhibition. HA 306-318 (SEQ ID NO: 4) inhibited both DR4 3838 and D3 T cell clones less efficiently (less than 60% inhibition) than it inhibited the DR1 3.19 and 19.3 clones. These data show that peptides of SEQ ID NO: 8, 15, 16, 18, and 27 were significantly better inhibitors of T cell response than the reference influenza virus hemagglutinin peptide HA 306-318. Peptides of SEQ ID NO: 15 and 27 were high level inhibitors both of HLA-DR-1- and -DR-4-restricted CII-specific T cells.

TABLE 4

Affinity of selected YEAK-related peptides for HLA-DR4 (DRB 1*0401) molecules determined by competition with biotinylated competitors HA306-318 and YEAK (µM)

| SEQ ID NO | peptide sequence | HA 306-318 | YEAK |
|---|---|---|---|
| 4 | APKYVKQNTLKLATA | 26.0 | 8.2 |
| 5 | AAAYAAAAAAKAAAA | 7.0 | |
| 6 | AEKYAAAAAAKAAAA | 6.5 | |
| 7 | AKEYAAAAAAKAAAA | 4.5 | |
| 10 | KEAYAAAAAAKAAAA | 4.5 | |
| 11 | AEEYAAAAAAKAAAA | 2.0 | |
| 12 | AAEYAAAAAAKAAAA | 3.2 | 1.6 |
| 13 | EKAYAAAAAAKAAAA | 3.3 | |
| 14 | AAKYEAAAAAKAAAA | 4.0 | |
| 15 | AAKYAEAAAAKAAAA | 1.8 | <1.0 |
| 16 | EAAYAAAAAAKAAAA | 5.0 | |
| 17 | EKKYAAAAAAKAAAA | 1.8 | |
| 18 | EAKYAAAAAAKAAAA | 4.4 | 3.0 |
| 21 | AKKYEAAAAAAAAAA | 2.2 | |
| 26 | AAEYKAAAAAAAAAA | 1.8 | |
| 28 | AAKYEAAAAAAAAAA | 1.2 | |
| 29 | AAKYAEAAAAAAAAA | 1.2 | |
| 32 | AEYAKAAAAAAAAAA | 3.0 | |
| 33 | AEKYAAAAAAAAAAA | <1.0 | |
| 35 | AYKAEAAAAAAAAAA | 1.3 | |
| 36 | AKYAEAAAAAAAAAA | 3.0 | |
| | YEAK | 2.5 | 20.0 |

The data in these examples, performed with each peptide at least in duplicate, show that of 32 unique synthetic peptides, several inhibited binding of HA 306-318 and YEAK to recombinant HLA-DR1 and -DR4 molecules. Peptides which inhibited binding of HA 306-318 or YEAK to HLA-DR1 or -DR4 molecules contained Y at the P1 position. The presence of E, A and K in various combinations on the N-terminal side of P1 did not seem to influence the affinity of the binding. Of the subsequent residues, K at P8 was important for inhibition of HA 306-318 but not of YEAK binding to HLA-DR1. In contrast to HLA-DR1, a larger number of peptides inhibited binding of both HA 306-318 and YEAK to HLA-DR4 molecules. These peptides contained Y at the position corresponding to P1 and either K or A at the position corresponding to P8, with no preferences for specific amino acids at other positions. The affinity of the HA 306-318 for recombinant HLA-DR4 was lower, and that of YEAK higher, than for HLA-DR1 molecules, similarly to the case observed with HLA-DR1 and -DR4 molecules purified human from blood. The binding of some of the biotinylated peptides to either HLA-DR1 or -DR4 was inhibited by CII 261-273, as well as by HA 306-318 and YEAK, showing that these peptides may compete for presentation to CII-reactive T cells, similar to the whole YEAK mixture. Peptides with an affinity close to or higher than that of the reference natural peptides or the YEAK-mixture are listed in Tables 3 and 4, for HLA-DR1 and HLA-DR4, respectively.

Several of the 15-mer peptides inhibited type II collagen-specific T cell clones. These peptides all had Y at the position corresponding to P1 and either K or A at the position corresponding to P8, with no other specific patterns. Further, peptide SEQ ID NO: 8 inhibited type II collagen-reactive T cells better than YEAK.

The results of the Examples that are the embodiments of the invention, that the individual components of Y, E, A and K or peptides have sequences that correspond to binding motifs for anchor positions fitting the particular HLA-DR molecule (Y at the position corresponding to P1) can act as effective therapeutic agents for autoimmune diseases, substituting for a mixture of random polypeptides. A pharmaceutical composition comprising a pure synthetic short polypeptide of identified sequence can have fewer side effects when administered to a subject than a mixture of polypeptides of random sequence. Further, a particular peptide sequences that is effective in binding to an HLA-DR molecule can be embedded into a longer sequence, for example, containing direct repeats of the peptide sequence or other molecules such as amino acid analogs, to increase stability in vivo or to impart other desirable properties. A pharmaceutical composition comprising a pure synthetic longer identified sequence can be most effective in having greatest efficacy and least toxicity.

What is claimed is:

1. An isolated synthetic peptide having a sequence selected from the group consisting of: AKEYAAAAAAKAAAA (SEQ ID NO: 7), AAEYAAAAAAKAAAA (SEQ ID NO: 12), AAKYAEAAAAKAAAA (SEQ ID NO: 15), and EAKYAAAAAAKAAAA (SEQ ID NO: 18), wherein the synthetic peptide binds to an MHC class II protein with higher affinity than a control peptide CII 261-273 (SEQ ID NO: 2) or HA 306-318 (SEQ ID NO: 1).

2. The isolated peptide according to any of the peptides of claim 1, in which the tyrosine (Y) has been substituted by a valine (V) or a phenylalanine (F), wherein the peptide has an amino acid sequence selected from the group of: AKEVAAAAAAKAAAA (SEQ ID NO: 61), AAEVAAAAAAKAAAA (SEQ ID NO: 62), AAKVAPAAAAKAAAA (SEQ ID NO: 63), and EAKVAAAAAAKAAAA (SEQ ID NO: 64) AKEFAAAAAAKAAAA (SEQ ID NO: 65), AAEFAAAAAAKAAAA (SEQ ID NO: 66), AAKFAEAAAAKAAAA (SEQ ID NO: 67), and EAKFAAAAAAKAAAA (SEQ ID NO: 68).

3. An isolated synthetic peptide having a sequence selected from the group consisting of: AEKYAAAAAAKAAAA (SEQ ID NO: 6), AKEYAAAAAAKAAAA (SEQ ID NO: 7), KEAYAAAAAAKAAAA (SEQ ID NO: 10), AEEYAAAAAAKAAAA (SEQ ID NO: 11), AAEYAAAAAAKAAAA (SEQ ID NO: 12), EKAYAAAAAAKAAAA (SEQ ID NO: 13), AAKYEAAAAAKAAAA (SEQ ID NO: 14), AAKYAEAAAAKAAAA (SEQ ID NO: 15), EAAYAAAAAAKAAAA (SEQ ID NO: 16), EKKYAAAAAAKAAAA (SEQ ID NO: 17), EAKYAAAAAAKAAAA (SEQ ID NO: 18), AKKYEAAAAAAAAAA (SEQ ID NO: 21), AAEYKAAAAAAAAAA (SEQ ID NO: 26), AAKYEAAAAAAAAAA (SEQ ID NO: 28), AAKYAEAAAAAAAAA (SEQ ID NO: 29), AEYAKAAAAAAAAAA (SEQ ID NO: 32), AEKAYAAAAAAAAAA (SEQ ID NO: 33), AYKAEAAAAAAAAAA (SEQ ID NO: 35), and AKYAEAAAAAAAAAA (SEQ ID NO: 36), wherein the synthetic peptide binds to an MHC class II protein with higher affinity than a control peptide CII 261-273 (SEQ ID NO: 2) or HA 306-318 (SEQ ID NO: 1).

4. The isolated peptide according to any of the sequences of claim 3, in which the tyrosine (Y) has been substituted by a valine (V) or a phenylalanine (F), wherein the peptide has an amino acid sequence selected from the group of: AEKVAAAAAAKAAAA (SEQ ID NO: 69), AKEVAAAAAAKAAAA (SEQ ID NO: 70), KEAVAAAAAAKAAAA (SEQ ID NO: 71), AEEVAAAAAAKAAAA (SEQ ID NO: 72), AAEVAAAAAAKAAAA (SEQ ID NO: 73), EKAVAAAAAAKAAAA (SEQ ID NO: 74), AAKVEAAAAAKAAAA (SEQ ID NO: 75), AAKVAEAAAAKAAAA (SEQ ID NO: 76), EAAVAAAAAAKAAAA (SEQ ID NO: 77), EKKVAAAAAAKAAAA (SEQ ID NO: 78), EAKVAAAAAAKAAAA (SEQ ID NO: 79), AKKVEAAAAAAAAAA (SEQ ID NO: 80), AAEVKAAAAAAAAAA (SEQ ID NO: 81), AAKVEAAAAAAAAAA (SEQ ID NO: 82), AAKVAEAAAAAAAAA (SEQ ID NO: 83), AEVAKAAAAAAAAAA (SEQ ID NO: 84), AEKVAAAAAAAAAAA (SEQ ID NO: 85), AVKAEAAAAAAAAAA (SEQ ID NO: 86), AKVAEAAAAAAAAAA (SEQ ID NO: 87), AEKFAAAAAAKAAAA (SEQ ID NO: 88), AKEFAAAAAAKAAAA (SEQ ID NO: 89), KEAFAAAAAAKAAAA (SEQ ID NO: 90), AEEFAAAAAAKAAAA (SEQ ID NO: 91), AAEFAAAAAAKAAAA (SEQ ID NO: 92), EKAFAAAAAAKAAAA (SEQ ID NO: 93), AAKFEAAAAAKAAAA (SEQ ID NO: 94), AAKFAEAAAAKAAAA (SEQ ID NO: 95), EAAFAAAAAAKAAAA (SEQ ID NO: 96), EKKFAAAAAAKAAAA (SEQ ID NO: 97), EAKFAAAAAAKAAAA (SEQ ID NO: 98), AKKFEAAAAAAAAAA (SEQ ID NO: 99), AAEFKAAAAAAAAAA (SEQ ID NO: 100), AAKFEAAAAAAAAAA (SEQ ID NO: 101), AAKFAEAAAAAAAAA (SEQ ID NO: 102), AEFAKAAAAAAAAAA (SEQ ID NO: 103), AEKAFAAAAAAAAAA (SEQ ID NO: 104), AFKAEAAAAAAAAAA (SEQ ID NO: 105), and AKFAEAAAAAAAAAA (SEQ ID NO: 106).

* * * * *

UNITED STATES PATENT AND TRADEMARK OFFICE
CERTIFICATE OF CORRECTION

PATENT NO. : 7,566,767 B2
APPLICATION NO. : 10/438538
DATED : July 28, 2009
INVENTOR(S) : Strominger et al.

Page 1 of 1

It is certified that error appears in the above-identified patent and that said Letters Patent is hereby corrected as shown below:

Claim 2, column 47, lines 39/40: delete "AAKVAPAAAAKAAAA" and insert --AAKVAEAAAAKAAAA--

Claim 4, column 48, line 36: delete "EAAVAAAAAKAAAA" and insert --EAAVAAAAAKAAAA--

Signed and Sealed this

Twenty-ninth Day of September, 2009

David J. Kappos
*Director of the United States Patent and Trademark Office*